United States Patent [19]

Westerman

[11] Patent Number: 4,634,591

[45] Date of Patent: Jan. 6, 1987

[54] ANTI-GAGGING COMPOSITIONS AND METHOD OF TREATING GAGGING REFLEXES

[76] Inventor: Robert D. Westerman, 7931 Jefferson Hwy., Baton Rouge, La. 70809

[21] Appl. No.: 773,055

[22] Filed: Sep. 6, 1985

[51] Int. Cl.⁴ ..................... A61K 38/06; A61K 33/10; A61K 33/14; A61K 33/20

[52] U.S. Cl. ................................... 424/149; 424/153; 424/154; 424/156

[58] Field of Search ................ 424/153, 154, 149, 156

[56] References Cited

U.S. PATENT DOCUMENTS 3,676,553  7/1972  Reynolds ........................... 424/153

OTHER PUBLICATIONS

Physicians' Desk Reference (PDR), Quarterly Supplement, Jul. 1966, p. 31.

*Primary Examiner*—Stanley J. Friedman
*Attorney, Agent, or Firm*—Abraham Friedman

[57] ABSTRACT

A method for controlling gagging in a patient susceptible to such reflexes in response to an oral procedure. The method is by administering to the patient prior to the onset of the gagging, a pharmaceutical composition comprising at least one of the electrolytes normally found in the human blood stream and/or gastric secretions. Preferably, the electrolytes should be provided in the same proportions as they are found in the blood stream and/or gastric secretions.

7 Claims, No Drawings

ANTI-GAGGING COMPOSITIONS AND METHOD OF TREATING GAGGING REFLEXES

BACKGROUND OF THE INVENTION

This invention relates to the controlling of gagging or retching reflexes in patients susceptible to such reactions in response to oral procedures.

In the course of examination or while being subjected to dental or oral procedures, a considerable number of individuals are susceptible to gagging or retching as a reflex action. Some individuals are so sensitive, that even utilizing a tongue depressor, or at home in response to flossing or brushing of one's teeth, they may also experience such gagging problems. While the degree of gagging may vary, the sensitivity to such oral procedures and the gagging or retching reflex is one that causes considerable discomfort and can often interfere with the efficient and effective performance of the procedure required.

The spasmodic movement of the patient in response to the oral procedure places the safety of the patient in jeopardy. It has therefore been considered to be highly desirable, and in some cases even imparative, to avoid the gagging reflex in such susceptible individuals in order to render dental or medical treatment more safe and efficient.

The cause of such gagging or retching varies with each patient, but can be classified under systemmic disorders, psychological factors, physiological factors, and iatrogenic factors. Systemmic disorders pertain to the patient's general health. Chronic gastrointestinal problems, blocked nasal passages, sinusitis, alcoholism, and various medications can often have a profound effect on a patient's gagging reflex. Iatrogenic factors pertain to the poor execution of intra-oral procedures by the dentist where various techniques and instruments may excite the gagging reflex. The underlying causes of gagging are usually attributed to psychologic and physiologic factors. Often these factors are hard to distinguish. Psychologic factors may consist of pre-conditioned reflexes from childhood or fear of the dental operation. Physiologic factors may be divided into extra-oral or intra-oral stimuli. Extra-oral stimuli include the sight of a mouth mirror, the taste of teeth cleaning compound, or hearing the dentist drill, any of which may initiate the gag reflex. The touching of sensitive areas of the mouth, tongue, and throat constitute intra-oral stimuli.

Various methods have been tried to manage overactive gagging reflexes. These include drug therapy such as barbiturates, atropine series drug, antihistamines, and topical anesthetics. Distracting agents have been tried such as snapping fingers and lifting of one's leg. Hypnosis and psychological conditioning have been attempted. Denture modifications have also been tried. However, none of these have attempted to control the basic problem of the gagging or retching and have all tried to combat the problem using indirect methods.

Accordingly, there is a great need for a simple and efficient method of controlling gagging in a patient susceptible to such reflexes in response to any oral procedure which may cause such stimulation.

SUMMARY OF THE INVENTION

It is accordingly an object of the present invention to provide a method of controlling gagging or retching in a patient susceptible to such response.

A further object of the present invention is to provide a method of controlling gagging or retching of a patient in response to an oral procedure which stimulates such reaction.

A further object of the present invention is to provide a method of preventing gagging or retching during oral procedures.

Still a further object of the present invention is to provide a method of treating or inhibiting gagging or retching in a patient susceptible to such reactions.

A further object of the present invention is to provide a method which may be readily applied to gag susceptible patients prior to their being subjected to a particular dental or oral procedure which will serve to condition the patient and stop or reduce or control this undesired reflex action.

A further object of the present invention is to provide a method whereby the gag reflex of susceptible individuals may be stopped, reduced, or controlled by means of commonly used innocuous substances in negligible quantities, and which will serve to achieve the foregoing effect upon the patient.

A further object of the present invention is to provide a method whereby a patient's gag reflex is controlled, reduced or stopped by the simple sublingual application of an effective composition in soluble tablet form.

Yet a further object of the present invention is to provide a method of controlling the gagging in a patient susceptible to such reflex by utilizing a sublingual tablet containing ingredients which are natural to the human body.

Another object of the present invention is to provide a method for controlling the gagging in a patient susceptible to such reflex, by application of a pharmaceutical composition comprising at least some of the electrolytes normally found in the human blood stream and/or stomach.

A further object of the present invention is to provide a composition containing a pharmaceutical formulation comprising an effective amount of a chemical for controlling a gagging reflex in a patient susceptible to such reflexes.

Yet a further object of the present invention is to provide a composition containing at least some of the electrolytes commonly found in the human blood stream and/or stomach in an effective amount for controlling a gagging reflex in a patient.

A further object of the present invention is to provide a composition containing a solid oral dosage in sublingual tablet form of at least some electrolytes commonly found in the human blood stream and/or stomach for controlling gagging or retching in a patient.

Briefly, in accordance with the present invention, there is provided a method for controlling gagging in a patient susceptible to such reflex by providing to the patient an effective amount of at least one of the electrolytes normally found in the human blood stream and/or stomach. Such electrolytes can include sodium, potassium, calcium, magnesium, chloride, bicarbonate, and phosphate.

The following objects, features and advantages of the invention will, in part, be pointed out with particularity, and will, in part, become obvious from the following more detailed description of the invention.

DESCRIPTION OF THE PREFERRED EMBODIMENT

The present invention provides for a method of controlling the gagging in a patient susceptible so such reflex in response to an oral procedure. The method includes providing to the patient a pharmaceutical composition comprising at least some of the electrolytes normally found in the human blood stream and/or in gastric secretions in human beings. The selected electrolytes are combined into a single soluble tablet in the same proportion as they are found in the blood stream and/or gastric secretions. The tablet is preferably administered sublingually shortly prior to the initiation of an oral procedure. The tablet may also be supplied for home use by individuals who cannot brush or floss their teeth properly because of the gagging problem.

The electrolytes which are typically found in blood chemistry include the following electrolytes in the following normal serum values:

| ELECTROLYTES | NORMAL SERUM VALUES mEq/l |
|---|---|
| Sodium | 136–145 |
| Potassium | 3.5–5.5 |
| Calcium | 4.5–5.5 |
| Magnesium | 1.8–3.6 |
| Chloride | 100–110 |
| Bicarbonate | 24–31 |
| Phosphate | 1.8–2.3 |

The electrolytes which are typically found in gastric secretions include the following electrolytes in the following normal values.

| ELECTROLYTES | NORMAL VALUES (mEq/l) | |
|---|---|---|
| | PARIETAL | NONPARIETAL |
| Hydrogen | 160 | — |
| Sodium | — | 160 |
| Potassium | 10 | 10 |
| Calcium | — | 4 |
| Chloride | 170 | 125 |

In order of importance, it has been found that use of Sodium, Chloride and Bicarbonate would be approximately 80-85% effective. Using Sodium, Chloride, Bicarbonate, Calcium and Potassium, the tablet would be 98% effective.

The tablet is normally provided in sublingual solid composition form. It is placed under the tongue of a susceptible patient and given 2–5 minutes for a substantial portion of the tablet to be dissolved and absorbed into the patient's system. The intra-oral procedures can then be started because efficacy is usually obtained within this period. If a person is a severe gagger, it may be necessary to follow with a second tablet in order to obtain the necessary result. The tablet has been found to work with excellent results. The tablet has been utilized in actual tests with a considerable number of patients. In none of them have there been any side effects, or follow up problems. All of the ingredients have been tested individually. They are safe, especially since the components are natural to the human body.

In a typical formation of the tablet, certain salts were selected which in their combination would produce the particular milliequivalents of the required electrolyte ions. The salts utilized were Sodium Chloride, Potassium Chloride, Calcium Chloride Calcium Lactate, Magnesium Sulfate, Sodium Bicarbonate, and Sodium Phosphate. These were to be combined to provide the proportions similar to those found in blood serum. The following formulas were utilized in calculating the amount of the salt required in order to provide the mulliequivalent of the ion:

$$W = M/(V \times N)$$

$$G = Q \times W$$

where:

M: Molecular weight of the salt
V: Valency of the ion
n: number of ions (cations or anions) in the molecule
W: weight of salt containing one milliequivalent of an ion.
Q: the required number of milliequivalents of the ion.
G: amount of salt needed to provide Q mEq of the ion.

The following table I shows the amount of each of the salts required in order to give the desired mulliequivalents of the ion which would be in the proper proportinate range as it presently found in blood serum:

TABLE I

| Salt | Milliequivalents of the ion Q | | | | | | | M | W (mg) | G (gms) | F (gms) |
|---|---|---|---|---|---|---|---|---|---|---|---|
| | $Na^+$ | $K^+$ | $Ca^{+2}$ | $Mg^{+2}$ | $Cl^-$ | $HCO_3^-$ | $HPO_4^-$ | | | | |
| 1. Sodium chloride | 100 | | | | 100 | | | 58.5 | 58.5 | 5.85 | 3.88 |
| 2. Potassium chloride | | 5 | | | 5 | | | 74.5 | 74.5 | 0.37 | 0.25 |
| 3. Calcium lactate | | | 5 | | | | | 308.3 | 154.0 | 0.77 | 0.51 |
| 4. Magnesium sulfate | | | | 2 | | | | 246.5 | 123.0 | 0.25 | 0.17 |
| 5. Sodium bicarbonate | 30 | | | | | 30 | | 84.0 | 84.0 | 2.52 | 1.67 |
| 6. Sodium phosphate | 6 | — | — | — | — | — | 3 | 268.1 | 134.0 | 0.80 | 0.53 |
| TOTAL | 136 | 5 | 5 | 2 | 105 | 30 | 3 | | | 10.56 | 7.00 |

Legend:
M: Molecular weight of the salt
W: Weight of the salt containing one milli-equivalent of m ion.
G: Amount of salt needed to provide Q mEq of the ion.
F: Amount of salt used in making the tablets.

In the preparation of tablet triturates, sucrose in the amount of 0.37 grams was added to the above 7 grams of the salts. The ingredients were pulverized in a procelain mortar and passed through a No. 60 mesh U.S. Standard sieve. The required amount of each ingredient was accurately weighed and transferred to a porcelain mortar. The materials were manually mixed for 10 minutes by a circular mixing motion of the pestle. An adequate amount of previously prepared hydroalcoholic excepient comprising 75% v/v alcohol was used to moisten the blended powders. The material was then molded into the proper shaped tablet. The tablets were then air dried overnight.

The various tablets were tested for weight variation, disintegration, and content uniformity. The results showed that the weight variation limits of the tablets were well within the required range outlined for medicinal compositions. Concerning the content uniformity, all of the tablets were tested and both the observed and theoretical values appeared in close agreement. The theoretical values represented the proportions in which the electrolytes were present in the blood stream, with the observed values also being in the same proportion as found in the blood stream. All the other tests proved the tablets to be in proper requirements for medicinal use and purposes.

The tablets were then tested on a number of patients and in each case the tablet was dissolved and found to suppress and stop the gag reflex in all of the patients.

There has been disclosed heretofore the best embodiment of the invention presently contemplated. However, it is to be understood that various changes and modifications may be made thereto without departing from the spirit of the invention.

What is claimed is:

1. A method for controlling gagging of a patient susceptible to such reflexes in response to an oral procedure, which comprises administering to such patient prior to the onset of such gagging a pharmaceutical composition comprising the following electrolytes normally present in the blood stream:

Sodium: 136–145 mEg/l
Potassium: 3.5–5.5 mEg/l
Calcium: 4.5–5.5 mEg/l
Magnesium: 1.8–3.6 mEg/l
Chloride: 100–110 mEg/l
Bicarbonate: 24–31 mEg/l
Phosphate: 1.8–2.3 mEg/l.

2. The method of claim 1, which comprises administering the pharmaceutical composition in a solid oral dosage from sublingually to the patient.

3. A method for preventing gagging or retching during oral procedures, which comprises administering sublingually to a patient experiencing such procedures a formulation comprising one or more compounds selected to produce the following electrolytes normally present in the blood stream;

Sodium: 136–145 mEg/l
Potassium: 3.5–5.5 mEg/l
Calcium: 4.5–5.5 mEg/l
Magnesium: 1.8–3.6 mEg/l
Chloride: 100–110 mEg/l
Bicarbonate: 24–31 mEg/l
Phosphate: 1.8–2.3 mEg/l.

4. A method of inhibiting gagging or retching reactions in a patient susceptible to such reactions, which comprises administering to the patient in need thereof an effective dosage of the following electrolytes normally present in the blood stream to provide an antigagging reaction:

Sodium: 136–145 mEq/l
Potassium: 3.5–5.5 mEq/l
Calcium: 4.5–5.5 mEq/l
Magnesium: 1.8–3.6 mEq/l
Chloride: 100–110 mEq/l
Bicarbonate: 24–31 mEq/l
Phosphate: 1.8–2.3 mEq/l.

5. The method of claim 4 which comprises administering the dosage in a solid oral form sublingually to the patient.

6. The method of inhabiting, gagging or retching reactions in a patient susceptible to such reactions, which comprises administering to the patient in need thereof an effective dosage of the following electrolytes normally present in gastric secretions to provide an antigagging reaction:

Hydrogen approximately 160 mEq/l
Potassium approximately 10 mEq/l
Chloride approximately 170 mEq/l.

7. The method of inhabiting, gagging or retching reactions in a patient susceptible of such reactions, which comprises administering to the patient in need thereof an effective dosage of the following electrolytes normally present in gastric secretions to provide an antigagging reaction:

Sodium approximately 160 mEq/l
Potassium approximately 10 mEq/l
Calcium approximately 4 mEq/l
Chloride approximately 125 mEq/l
Bicarbonate approximately 45 mEq/l
Phosphate approximately 6 mEq/l.

* * * * *